United States Patent [19]

Trawöger et al.

[11] Patent Number: 5,613,851
[45] Date of Patent: Mar. 25, 1997

[54] SEPARATOR FOR A DENTAL SUCTION APPARATUS

[76] Inventors: Werner Trawöger, Huebe 26; Bruno Pregenzer, Huebe 30, both of A-6173 Oberperfuss, Austria

[21] Appl. No.: 495,440

[22] PCT Filed: Nov. 4, 1994

[86] PCT No.: PCT/AT94/00165

§ 371 Date: Sep. 11, 1995

§ 102(e) Date: Sep. 11, 1995

[87] PCT Pub. No.: WO95/12365

PCT Pub. Date: May 11, 1995

[30] Foreign Application Priority Data

Nov. 5, 1993 [AT] Austria ................................. 2244/93

[51] Int. Cl.⁶ ................................................. A61C 17/06
[52] U.S. Cl. .................................................... 433/92
[58] Field of Search ............................ 433/92; 210/512.1, 210/512.3, 188, 787

[56] References Cited

U.S. PATENT DOCUMENTS

| | | | |
|---|---|---|---|
| 4,564,374 | 1/1986 | Hoffmann | 433/92 X |
| 5,018,971 | 5/1991 | Trawoger et al. | 433/92 |
| 5,330,641 | 7/1994 | Cattani | 433/92 X |

FOREIGN PATENT DOCUMENTS

89/04152  5/1989  WIPO.

Primary Examiner—Jeffrey A. Smith
Attorney, Agent, or Firm—Herbert L. Lerner; Laurence A. Greenberg; Werner H. Stemer

[57] ABSTRACT

A separator for a suction air-solid-liquid mixture in a dental suction apparatus has an intermediate container situated beneath an air separation chamber, which has an outlet for the separated mixture. Associated with and situated along side the mixture outlet, a separation device for the solids has a removable sedimentation basin and a clean liquid outlet through which the clean liquid is conveyed into the intermediate container. A tube connecting with the second segment of the suction line passes through the intermediate container from the air separation chamber and has a clean liquid admission port so that the solids-free liquid is fed back into the suction air.

4 Claims, 2 Drawing Sheets

SEPARATOR FOR A DENTAL SUCTION APPARATUS

BACKGROUND OF THE INVENTION

Field of the Invention

The invention pertains to a separator for separating an air-solids-liquid mixture in a dental suction apparatus, whereby the suction apparatus has a suction pump, a suction nozzle aspirating the mixture from the mouth of a patient, and a suction line extending between the suction nozzle and the suction pump, which suction line is divided into two segments by the separator, with an air separation chamber connectible to the first segment of the suction line and provided with deflection surfaces, which air separation chamber is provided with a clean air outlet connectible to the second segment of the suction line and an outlet for the separated mixture, with a separation device for solid matter assigned to the mixture outlet, which separation device has a removable sedimentation container and a clean liquid outlet, and with a device for feeding the clean liquid into the second segment of the suction line which has an intermediate container connected with the clean liquid outlet.

Separators of this kind are for instance needed in dentist's processing systems when the central suction pump is formed by a liquid seal pump, which requires a feed of liquid for equalizing losses in the water ring, or when the separator is to be integrated into an existing system, the suction pump of which has a suction air-liquid separator connected upstream thereof whose functionality must be retained. A separator which is suitable for this and which may also have a centrifuge for solid matter separation, is described in U.S. Pat. No. 5,018,971, whereby the intermediate container collecting the clean liquid and sedimenting possibly remaining solid matter, and the supply device for clean liquid which, in particular, has a Venturi pipe, is shown in the second segment of the suction line essentially schematically at an arbitrary location.

SUMMARY OF THE INVENTION

The invention is thus based on the object to form such a separator as a structurally compact, space-saving apparatus, which can be integrated in a known manner in situ.

This is attained, in accordance with the invention, in that the intermediate container is disposed below the air separation chamber and that both are commonly provided laterally adjacent the solid matter separation device, and in that the clean air outlet of the air separation chamber is provided at a tube which is connectible with the second segment of the suction line, which tube extends through the intermediate container and which has a clean liquid admission port. This construction leads to a compact structure which has an air treatment station and a solid matter treatment station next to one another. On the input side of the air treatment station the air is separated off and on the outlet side the liquid is added which has been separated from the solid matter in the solid matter treatment station. The solid matter treatment station can—because it extends above the height of the air separation chamber and the clean liquid supply device—comprise a centrifuge, whereby in this preferred embodiment the sedimentation container is disposed below the solid bowl centrifuge and laterally adjacent the intermediate container and communicates with the mixture outlet of the air separation chamber as well as with the sludge outlet of the centrifuge, and that a device is provided for supplying into the centrifuge the liquid collecting in the sedimentation container and containing residual solid matter.

The mixture outlet of the air separation chamber and/or of the clean liquid inlet of the preferably also removable intermediate container and/or the end of the tube extending through the intermediate container are each preferably provided laterally.

The invention will in the following be described with the aid of the figures of the enclosed drawings, without being limited thereto.

DESCRIPTION OF THE PREFERRED EMBODIMENT

Figure 1:
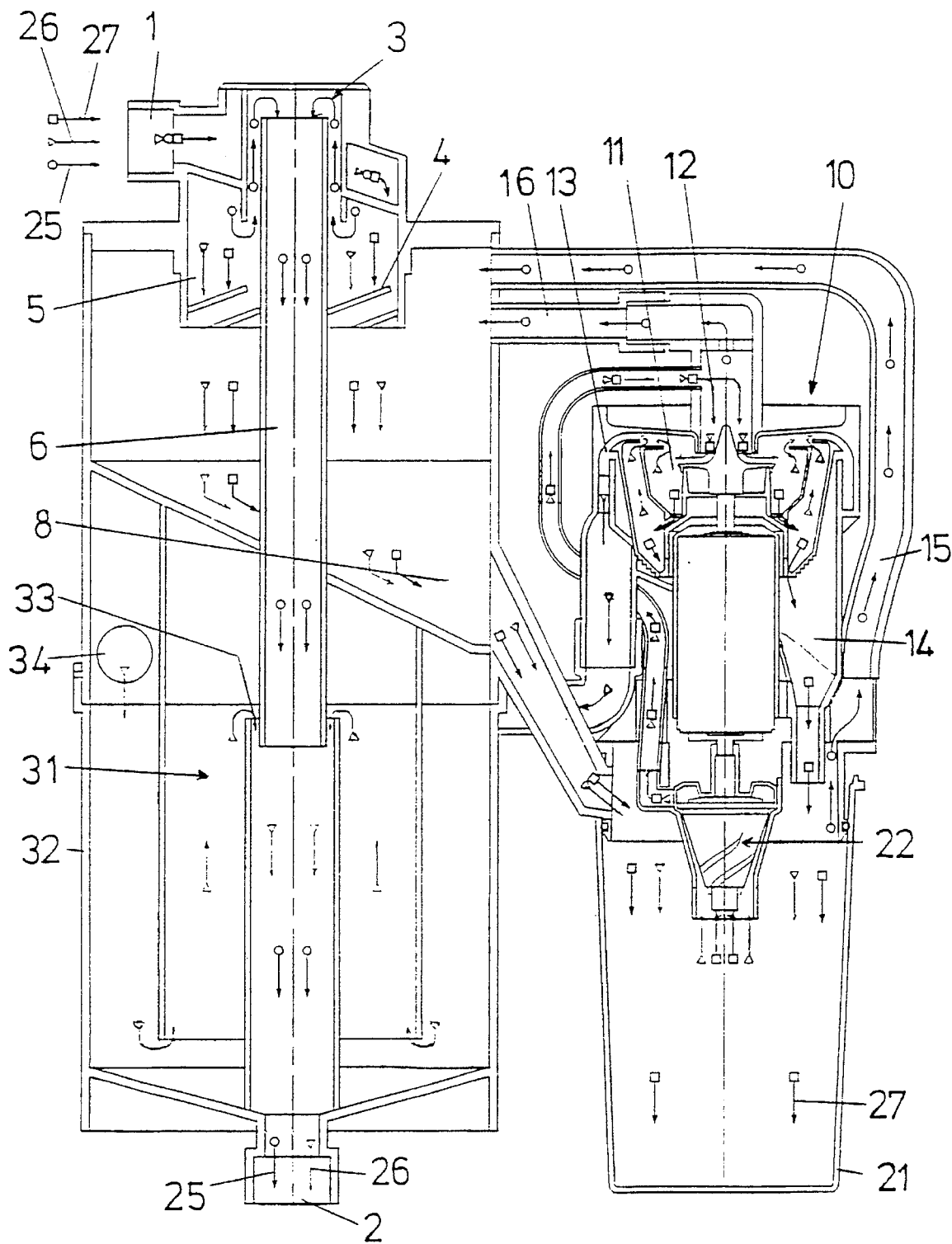
FIGS. 1 and 2 show schematic vertical sections through two different exemplary embodiments of the separator.

The separator is inserted into a suction line which supplies to the separator via its first segment 1 an air-liquid-solid matter mixture 25, 26, 27 aspirated from the mouth of a patient and which transports off a cleaned air-liquid mixture 25, 26 via its second segment 2 leading to the suction pump. When the pump consists of a liquid seal pump, then the cleaned air-liquid mixture can be directly supplied thereto, whereby the liquid can replace the water ring losses. The separator comprises an air treatment station which is connectible with the two segments 1, 2 of the suction line and a solid matter separation device 10 disposed laterally adjacent thereto. The air treatment station has an air separation chamber 5 provided with deflector surfaces 4 and/or a cyclone configuration, and below the separation chamber there is disposed an intermediate container 32 provided with a clean liquid supply device 31, into which intermediate container clean liquid 26 flows from the solid matter separation device 10 via an inlet 34. The suction air 25 separated in the air separation chamber 5 leaves the same through a tube 6, which is connectible to the second segment 2 of the suction line and which extends through the intermediate container 32, whereby the clean air outlet 3 of the air separation chamber 5 is provided at the upper air admission port of the tube 6 disposed inside the deflector surface 4. A clean liquid admission port 33 is formed in the region of the tube 6 extending through the intermediate container 32.

An outlet 8 extends obliquely downwardly in the lower air separation chamber 5 for the mixture 26, 27 freed of air 25 into a sedimentation container 21 of the solid matter separation device 10, which is removably disposed at the lower side of a solid bowl centrifuge 11. A device 22 is assigned to the solid bowl centrifuge 11 which feeds the liquid 26 collecting above the solid matter 27 sedimenting in the sedimentation container 21 and remaining solid matter to the upper mixture admission port 12, whereby the device 22 in particular comprises a pump which is driven commonly with the centrifuge. The clean liquid 26 separated in the centrifuge 11 leaves the same through the upper clean liquid outlet 13 and exits through the inlet 34 into the intermediate container 32. At stillstand of the centrifuge 11, the solid matter separated therein together with the remaining liquid flows through the lower sludge outlet 14 into the sedimentation container 21, in which the solid matter sediments, and from which remaining liquid, together with liquid following via the mixture outlet 8 and remaining solid matter, is fed back to the mixture admission port 12 of the centrifuge 11. Since the complete separator is disposed in the vacuum of the suction pump, air compensation lines 15 and 16 are provided between the sedimentation container 21 as well as the mixture inlet 12 of the centrifuge 11 and the air separation chamber 5. A possible spit bowl drain may be effected through the first segment of the suction line, when the spit bowl is connected to the suction line in the form of a movable funnel, or through an appropriate valve control into the air separation chamber 5, into the sedimentation container 21 or into the mixture inlet 12 of the centrifuge.

Figure 2:
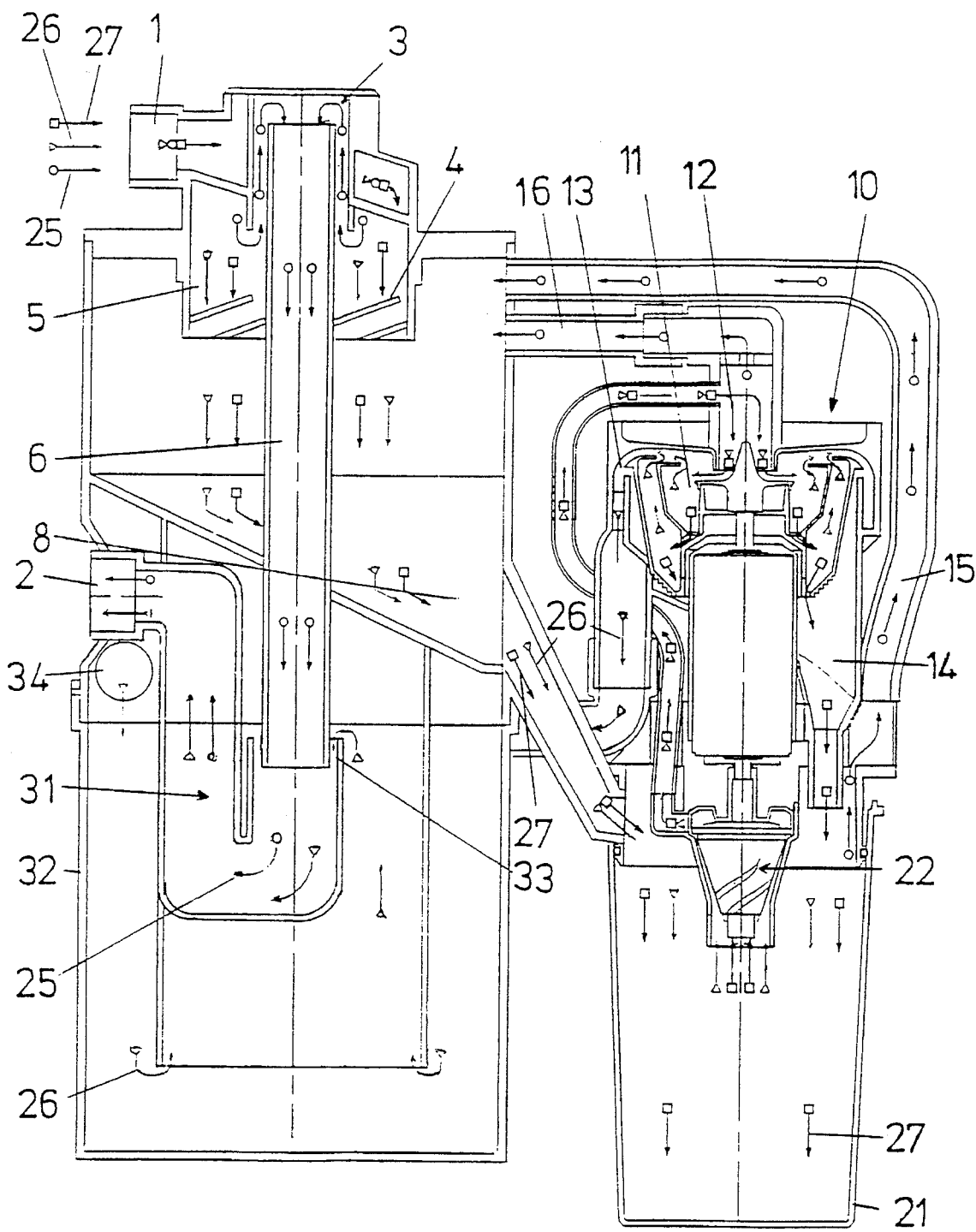

In the embodiment according to FIG. 1 there is provided the connection of the tube 6 at the second segment of the suction line at the floor of the intermediate container 32. According to FIG. 2, the tube 6 leads back upwardly and the connection is formed laterally, directly below the air separation chamber 5. In this embodiment, the intermediate container 32, which is also removably formed and into which still remaining solid matter can sediment from the clean liquid, is better accessible, because it can be removed downwardly without an interruption of line connections similarly to the sedimentation container 21.

We claim:

1. In a dental suction apparatus having a separator for separating an air-solids-liquid mixture of the type comprising:

a suction pump, a suction nozzle aspirating the mixture from a mouth of a patient, and a suction line extending between the suction nozzle and the suction pump, and a separator disposed in the suction line and dividing the suction line into first and second segments;

said separator having an air separation chamber formed therein with deflector surfaces, said air separation chamber being formed with a clean air outlet connectible to the second segment of the suction line and an outlet for a separated mixture;

a solid matter separation device communicating with the outlet for the separated mixture, said solid matter separation device comprising a removable sedimentation container and being formed with a clean liquid outlet; and a device for feeding the clean liquid into the second segment of the suction line comprising an intermediate container communicating with the clean liquid outlet of the solid matter separation device;

the improvement which comprises:

said intermediate container being disposed below said air separation chamber, and said intermediate container and said air separation chamber together being disposed laterally adjacent said solid matter separation device; and and a tube communicating with said clean air outlet formed in said air separation chamber and being connectible to the second segment of the suction line, said tube extending through said intermediate container and being formed with a clean liquid admission port.

2. The separator according to claim 1, wherein said solid matter separation device includes a solid bowl centrifuge for separating solid matter, said centrifuge being formed with an upper clean liquid outlet and a lower sludge outlet, including a sedimentation container disposed below the solid bowl centrifuge and laterally adjacent said intermediate container, said sedimentation container communicating with the mixture outlet of said air separation chamber and with the sludge outlet of the centrifuge, and a centrifuge feed device for supplying into the centrifuge solid-matter containing liquid collecting in said sedimentation container.

3. A separator for a dental suction apparatus of the type having a pump, a suction line aspirating an air-solids-liquid mixture from the mouth of a patient, and the separator being disposed in the suction line and dividing the suction line in first and second segments, the separtor comprising:

means defining an air separation chamber with deflector surfaces formed therein, said air separation chamber being formed with a clean air outlet connectible to the second segment of the suction line and an outlet for a separated mixture;

a solid matter separation device communicating with the outlet for the separated mixture, said solid matter separation device including a removable sedimentation container and being formed with a clean liquid outlet;

an intermediate container disposed below said air separation chamber and communicating with the clean liquid outlet of said solid matter separation device for feeding the clean liquid into the second segment of the suction line; said intermediate container and said air separation chamber together being disposed laterally adjacent said solid matter separation device; and and a tube communicating with said clean air outlet formed in said air separation chamber and being connectible to the second segment of the suction line, said tube extending through said intermediate container and being formed with a clean liquid admission port.

4. The separator according to claim 3, wherein said solid matter separation device includes a solid bowl centrifuge for separating solid matter, said centrifuge being formed with an upper clean liquid outlet and a lower sludge outlet, and further including a sedimentation container disposed below said solid bowl centrifuge and laterally adjacent said intermediate container, said sedimentation container communicating with the mixture outlet of said air separation chamber and with the sludge outlet of the centrifuge, and a centrifuge feed device for supplying into said centrifuge solid-matter containing liquid collecting in said sedimentation container.

* * * * *